United States Patent [19]

Balbierz et al.

[11] Patent Number: 5,156,596
[45] Date of Patent: Oct. 20, 1992

[54] CATHETER WITH CHANGEABLE NUMBER OF LUMENS

[75] Inventors: Daniel J. Balbierz, Redwood City; Joseph R. Thomas, San Carlos, both of Calif.

[73] Assignee: Menlo Care, Inc., Menlo Park, Calif.

[21] Appl. No.: 650,439

[22] Filed: Feb. 4, 1991

[51] Int. Cl.$^5$ ............................................. A61M 5/178
[52] U.S. Cl. .................................. 604/164; 604/167; 604/264
[58] Field of Search .................. 604/93, 158, 164, 167, 604/244, 245, 246, 264, 280, 283, 284, 905

[56] References Cited

U.S. PATENT DOCUMENTS

| | | |
|---|---|---|
| Re. 31,873 | 4/1985 | Howes . |
| 4,037,599 | 7/1977 | Raulerson ........................ 604/283 |
| 4,072,146 | 2/1978 | Howes . |
| 4,099,528 | 7/1978 | Sorenson et al. ................. 604/164 |
| 4,224,943 | 9/1980 | Johnson et al. .................. 604/164 |
| 4,327,723 | 5/1982 | Frankhouser . |
| 4,387,879 | 6/1983 | Tauschinski . |
| 4,406,656 | 9/1983 | Hattler et al. . |
| 4,417,886 | 11/1983 | Frankhouser et al. . |
| 4,447,236 | 5/1984 | Quinn . |
| 4,464,171 | 8/1984 | Garwin . |
| 4,493,696 | 1/1985 | Uldall . |
| 4,496,348 | 1/1985 | Genese et al. .................... 604/167 |
| 4,511,359 | 4/1985 | Vaillancourt . |
| 4,512,766 | 4/1985 | Vailancourt ..................... 604/169 |
| 4,525,157 | 6/1985 | Vaillancourt . |
| 4,531,937 | 7/1985 | Yates ................................ 604/164 |
| 4,559,043 | 12/1985 | Whitehouse et al. . |
| 4,652,256 | 3/1987 | Vaillancourt . |
| 4,655,750 | 4/1987 | Vaillancourt . |
| 4,668,225 | 5/1987 | Russo et al. ...................... 604/264 |
| 4,726,374 | 2/1988 | Bales et al. . |
| 4,737,146 | 4/1988 | Amaki et al. . |
| 4,745,950 | 5/1988 | Mathieu ............................ 604/905 |
| 4,772,264 | 9/1988 | Cragg . |
| 4,842,591 | 6/1989 | Luther . |
| 4,846,812 | 7/1989 | Walker et al. .................... 604/280 |
| 4,863,431 | 9/1989 | Vaillancourt . |
| 4,894,052 | 1/1990 | Crawford . |
| 4,917,668 | 4/1990 | Haindl ............................... 604/167 |
| 4,935,008 | 6/1990 | Lewis, Jr. .......................... 604/164 |
| 4,935,010 | 6/1990 | Cox et al. ......................... 604/167 |
| 5,006,114 | 4/1991 | Rogers et al. ..................... 604/167 |
| 5,021,044 | 6/1991 | Sharkawy .......................... 604/164 |

FOREIGN PATENT DOCUMENTS

| | | | |
|---|---|---|---|
| 139040 | 5/1985 | European Pat. Off. ............ 604/264 |
| 1284537 | 8/1972 | United Kingdom ................ 604/283 |

OTHER PUBLICATIONS

The Arrow Multi-Lumen Catheter System.

Primary Examiner—Gene Mancene
Assistant Examiner—Frank A. LaViola
Attorney, Agent, or Firm—Fliesler, Dubb, Meyer & LoveJoy

[57] ABSTRACT

A catheter assembly is provided. An attachment structure has a proximal end portion of an outer cannula attached to it. A needle is insertable through the outer cannula and the attachment structure. An inner cannula is attached to an inner cannula attachment region of the attachment structure. The inner cannula is insertable axially through the attachment structure. The attachment structure can comprise two hubs, one for the outer cannula and the other for the inner cannula, the two hubs being attachable to one another to form the overall attachment structure. A valve structure is associated with the attachment structure, suitably with the outer cannula hub. The valve structure normally closes communication between an access passage in the attachment structure, e.g., in the outer cannula hub, and the outer cannula lumen. The valve structure opens sufficiently for the inner cannula to pass through it and to open communication between the access passage and the outer cannula lumen when the inner cannula is inserted through another passage in the attachment structure and through the outer cannula lumen. The assembly allows the removal of the inner cannula and the insertion of a replacement inner cannula, if desired, without removing the outer cannula from the blood vessel. Use of a relatively small diameter needle for a desired diameter outer cannula can also be provided if the material of the outer cannula is such that it will swell in place.

44 Claims, 5 Drawing Sheets

CATHETER WITH CHANGEABLE NUMBER OF LUMENS

TECHNICAL FIELD

The present invention relates to a catheter assembly which includes an outer cannula which is insertable into a body conduit such as a vein. The number of lumens through which samples can be drawn, medicaments introduced or test probes can be inserted can be varied by the physician without removing the outer cannula from the blood vessel. In one embodiment the outer cannula is insertable utilizing an over-the-needle (as opposed to the over the wire) insertion technique.

BACKGROUND OF THE INVENTION

Currently there is a need for multi-lumen catheters for a variety of therapies where multiple drug injections are required. Unfortunately, current multi-lumen catheters are positioned in place utilizing a procedure which is bloody, complicated and potentially hazardous to both the patient and the practitioner, especially during central venous catheterization.

A problem with current catheter systems is that once they have been inserted they must be completely removed and replaced if one wants to have more (or less) or cleaner lumens. Thus, a messy and uncomfortable procedure may have to be repeated on a patient whose body is already under stress.

Another problem with existing multi-lumen catheters is that all of the method of inserting them cause blood loss that is dangerous to both the patient and the practitioner. The most common method is to utilize a needle to locate and pierce the blood vessel. A guide wire is then inserted through the needle into the blood vessel. The needle is then removed leaving the guide wire in place. The insertion site if often enlarged by sliding a dilator sheath down the guide wire to stretch open the skin and the vessel wall. The multi-lumen catheter is then slid along over the guide wire and through the now enlarged opening formed by the dilator sheath. Once the catheter has reached the proper location the guide wire and the dilator sheath are removed. The dilator sheath must be removed because its size and stiffness are a potential cause of serious injury (perforation, irritation) to the blood vessel.

Another current alternative is to directly expose and partially transect a vein whereby the catheter may be directly inserted into the vein. This can be a very bloody procedure and infection can easily set in.

As mentioned above, another problem with current multi-lumen catheters of the nature disclosed above is that if one wishes to change from, for example, a two lumen catheter to a three lumen catheter, or if one wishes to change the size of the lumens, this can only be accomplished by removing the catheter which is in place and replacing it with another catheter utilizing one of the above mentioned bloody and dangerous techniques.

A catheter system marketed by Arrow International, Inc. under the trademark Arrow-Flex allows for the insertion and removal of an inner cannula through a septum and through the lumen of an outer cannula. This system is, however, designed only for a very short term of use (during an operation) and can only be left in place at great risk to the patient. The outer cannula is made from a stiff polymer to aid in the forceful insertion procedure required to stretch the skin and blood vessel. Also, any liquids being flowed through the outer cannula lumen (i.e., through the annular space between the inner and outer cannulae) must be introduced downstream of the septum whereby the space immediately downstream of the septum (and upstream of the introduction of the liquid) is substantially stagnant. Furthermore, the fact that this space is not flushed out means that if the fluid being flowed through the outer cannula lumen is changed, there will be a transition time during which a mixture of the old and new fluids will be present. As some medicaments are not compatible with others such mixing can be undesirable.

Yet further, the multi-lumen catheters of the prior art have generally been fabricated of materials which are relatively stiff in order to allow them to be inserted and which thereafter remain relatively stiff while they are within the patient's body. As a result, these catheters can cause perforation of major veins which can result in death. For this reason these types of catheters are removed as soon as possible and replaced with softer catheters for the ongoing delivery of medicaments.

The present invention is directed to overcoming one or more of the problems as set forth above.

DISCLOSURE OF INVENTION

One embodiment of the invention is in the nature of an over-the-needle insertable multi-lumen catheter assembly. The assembly comprises an attachment structure having proximal and distal end regions, first and second internal passages which join one another at a junction region to form a distal exit passage, an outer cannula attachment region of a size and construction sufficient to allow a needle to be inserted therethrough, an inner cannula attachment region, a first proximal access region providing access to the first passage, a second proximal access region providing access to the second passage and an exit passage access region providing access to the distal exit passage. The assembly also includes an outer cannula having proximal and distal end portions and an outer cannula lumen, the proximal end portion of the outer cannula being attached to the outer cannula attachment region, the outer cannula lumen being of a size sufficient to allow the needle (and if desired an intermediate dilator) to be inserted therethrough. Also included is an inner cannula having proximal and distal end portions and an inner cannula lumen, the proximal end portion of the inner cannula being attached to the inner cannula attachment region in such a manner as to block fluid flow communication between the first proximal access region and the outer cannula lumen, the inner cannula being insertable axially through the first passage and the outer cannula lumen, the inner cannula being of a construction lumen, the inner cannula being of a construction such that when inserted into the outer cannula lumen it does not prevent flow therethrough. In addition there is valve means associated with the attachment structure for closing communication between the second passage and the outer cannula lumen, the valve means being openable sufficiently for the inner cannula to pass therethrough and to open up communication between the second passage and the outer cannula lumen.

In accordance with another embodiment of the invention a catheter structure is set forth with which the number of available lumens can be changed without removal from a patient's body. The catheter structure comprises an outer cannula hub having proximal and distal end portions, a passageway therethrough from the distal to the proximal end portion thereof and an outer cannula attachment region. Also present is an inner cannula hub having proximal and distal end portions, a first internal passage therethrough from the distal to the proximal end portion thereof and a second internal passage which joins the first internal passage at a junction region, an inner cannula attachment region, the distal end portion of the inner cannula hub being releasably couplable to the proximal end portion of the outer cannula hub with the first internal passage in the inner cannula hub in communication with the passageway through the outer cannula hub. Also provided is an outer cannula having proximal and distal end portions and an outer cannula lumen, the proximal end portion of the outer cannula being attached to the outer cannula attachment region so that the outer cannula extends distally from the outer cannula hub. Further included is an inner cannula attached to the inner cannula attachment region in such a manner as to block fluid flow communication between the proximal and distal end portions of the first passage, the inner cannula having proximal and distal end portion, the distal end portion thereof being insertable through the passageway in the outer cannula hub from the proximal end portion thereof and out of the distal end portion thereof. The catheter structure additionally includes an elastomeric septum having a self-sealing opening therethrough associated with the outer cannula hub for closing communication between the second passage and the outer cannula lumen, the distal end portion of the inner cannula being insertable through the opening through the septum. Furthermore, inner cannula sheathing means are provided for preventing the septum from exerting inward radial pressure on the inner cannula when the inner cannula distal end portion is inserted through the opening in the septum, the sheathing means also providing communication between the second passage in the inner cannula hub and the outer cannula lumen.

In accordance with another embodiment yet of the invention a catheter structure is set forth with which the number of available lumens can be changed without removal from a patient's body. The catheter structure comprises an outer cannula hub having proximal and distal end portions, a passageway therethrough from the distal to the proximal end portion thereof and an outer cannula attachment region. Also present is an outer cannula hub having proximal and distal end portions, a first internal passage therethrough from the distal to the proximal end portion thereof and a second internal passage which joins the first internal passage at a junction region, an inner cannula attachment region, the distal end portion of the inner cannula hub being releasably couplable to the proximal end portion of the outer cannula hub with the first internal passage in the inner cannula hub in communication with the passageway through the outer cannula hub. Also provided is an outer cannula having proximal and distal end portions and an outer cannula lumen, the proximal end portion of the outer cannula being attached to the outer cannula attachment region so that the outer cannula extends distally from the outer cannula hub. Further included is an inner cannula attached to the inner cannula attachment region in such a manner as to block fluid flow communication between the proximal and distal end portions of the first passage, the inner cannula having proximal and distal end portion, the distal end portion thereof being insertable through the passageway in the outer cannula hub from the proximal end portion thereof and out the distal end portion thereof. The catheter structure additionally includes an elastomeric septum having a self-sealing opening therethrough associated with the outer cannula hub which serves for closing communication between the second passage and the outer cannula lumen, the distal end portion of the inner cannula being insertable through the opening through the septum. An opening member is provided along with positioning means for positioning the opening member in the opening through the septum. The second passage in the inner cannula hub communicates with the outer cannula lumen responsive to positioning of the opening member in the opening in the septum. The opening member also prevents the septum from exerting inward radial pressure on the inner cannula when the inner cannula distal end portion is inserted through the opening in the septum.

Yet another embodiment of the invention is a catheter structure which comprises an attachment structure having proximal and distal end regions, first and second internal passages which join one another at a junction region to form a distal exit passage, an outer cannula attachment region, an inner cannula attachment region, a first proximal access region providing access to the first passage, a second proximal access region providing access to the second passage and an exit passage access region providing access to the distal exit passage. The catheter structure further comprises an outer cannula having proximal and distal end portions and an outer cannula lumen and being formulated of a material that softens with a softening ratio of greater than 2:1, the proximal end portion of the outer cannula being attached to the outer cannula attachment region. Also included is an inner cannula having proximal and distal end portions and an inner cannula lumen and being formulated of a material that softens with a softening ratio of greater than 2:1, the proximal end portion of the inner cannula being attached to the inner cannula attachment region in such a manner as to block fluid flow communication between the proximal and distal end portions of the first passage, the inner cannula being insertable axially through the first proximal access region and the first passage. Further provided is valve means associated with the attachment structure for closing communication between the second passage and the outer cannula lumen, the valve means being openable sufficiently for the distal end portion of the inner cannula to pass therethrough and to open communication between the second passage and the outer cannula lumen.

Still another embodiment of the invention is a catheter assembly comprising an outer cannula hub having proximal and distal end portions and defining a central longitudinal passageway therethrough having proximal and distal end portion, the passageway extending from the outer cannula hub proximal end portion to the outer cannula hub distal end portion. The assembly includes an outer cannula having proximal and distal end portions and defining an outer cannula lumen extending from the outer cannula proximal end portion to the outer cannula distal end portion, the outer cannula proximal end portion being attached to the outer cannula hub with the outer cannula lumen in flow communication with the outer cannula hub passageway. The assembly also includes an inner cannula hub having proximal and distal end portions and defining first and second passageways therethrough. Also present is an inner cannula having proximal and distal end portions and defining an inner cannula lumen extending from the inner cannula proximal end portion to the inner cannula distal end portion, the inner cannula proximal end portion being attached to the inner cannula hub with the inner cannula lumen in flow communication with the inner cannula hub first passageway and such that fluid flow from the inner cannula hub first passageway can only proceed through the inner cannula lumen. Attaching means are provided for detachably attaching the inner cannula hub to the outer cannula hub with the inner cannula positioned within and extending longitudinally along the outer cannula lumen. In addition, valve means is associated with the outer cannula hub for blocking communication between the proximal end portion of the outer cannula hub passageway and the outer cannula lumen, the valve means being openable in response to the inner cannula hub being attached to the outer cannula hub, the valve means, when opened, providing flow therethrough from the inner cannula hub second passageway to the outer cannula lumen.

A further embodiment yet of the invention is a catheter structure with which the number of available lumens can be changed without removal from a patient's body. The embodiment comprises an outer cannula hub having proximal and distal end portions, a passageway therethrough from the distal to the proximal end portion thereof and an outer cannula attachment region. The embodiment also includes an inner cannula hub having proximal and distal end portions, a first internal passage therethrough from the distal to the proximal end portion thereof and a second internal passage which joins the first internal passage at a junction region, an inner cannula attachment region, the distal end portion of the inner cannula hub being releasably couplable to the proximal end portion of the outer cannula hub with the first internal passage in the inner cannula hub in communication with the passageway through the outer cannula hub. Also present is an outer cannula having proximal and distal end portions and an outer cannula lumen, the proximal end portion of the outer cannula being attached to the outer cannula attachment region so that the outer cannula extends distally from the outer cannula hub. Additionally, an inner cannula is attached to the inner cannula attachment region in such a manner as to block off fluid flow communication between the proximal and distal end portions of the first passage, the inner cannula having proximal and distal end portions, the distal end portion thereof being insertable through the passageway in the outer cannula hub from the proximal end portion thereof and out of the distal end portion thereof. Also, an elastomeric septum is present having a self-sealing opening therethrough associated with the outer cannula hub for closing communication between the second passage and the outer cannula lumen, the distal end portion of the inner cannula being insertable through the opening through the septum. An opening member is provided which is adapted to open the opening in the septum when positioned therein. Moving means serve for moving the opening member into the opening in the septum and thereby providing fluid flow communication between the second passage and the outer cannula lumen.

The catheter structures of the present invention have a number of advantages over prior art devices. A very significant advantage is that one can change the number and size of the lumens without withdrawing the cannula from the patient's blood vessel. Another very significant advantage is the fact that the cannula can be made to be insertable in an over-the-needle fashion. This means that for the same diameter cannula one can utilize a smaller needle and can, in fact, make a smaller puncture wound in a blood vessel. Furthermore, if one uses a softening outer cannula in accordance with a preferred embodiment of the present invention, of softening outer and inner cannulae, the catheter structure can be left in place for relatively long periods of time due to the reduced potential of damaging the vessel when utilizing the softenable cannulae. Still further, if one utilizes a catheter structure in accordance with a preferred embodiment of the present invention which has both its inner and outer lumen swell when it is inserted in a blood vessel, one can utilize a still smaller needle thus significantly further reducing trauma. And, construction of a catheter assembly in accordance with the present invention is relatively inexpensive and simple.

BRIEF DESCRIPTION OF THE DRAWINGS

The invention will be better understood by reference to the figures of the drawings wherein like numbers denote like parts through and wherein.

BEST MODE FOR CARRYING OUT INVENTION

Figure 1:
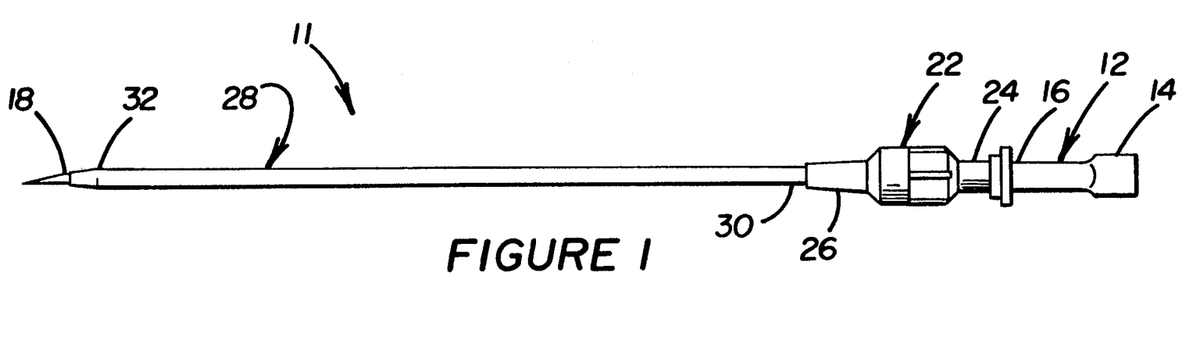
FIG. 1 illustrates, in side elevational view, an assembly which includes an outer cannula attached to an outer cannula hub, a needle and a needle hub, all for inserting an over-the-needle cannula in a blood vessel.
Figure 2:
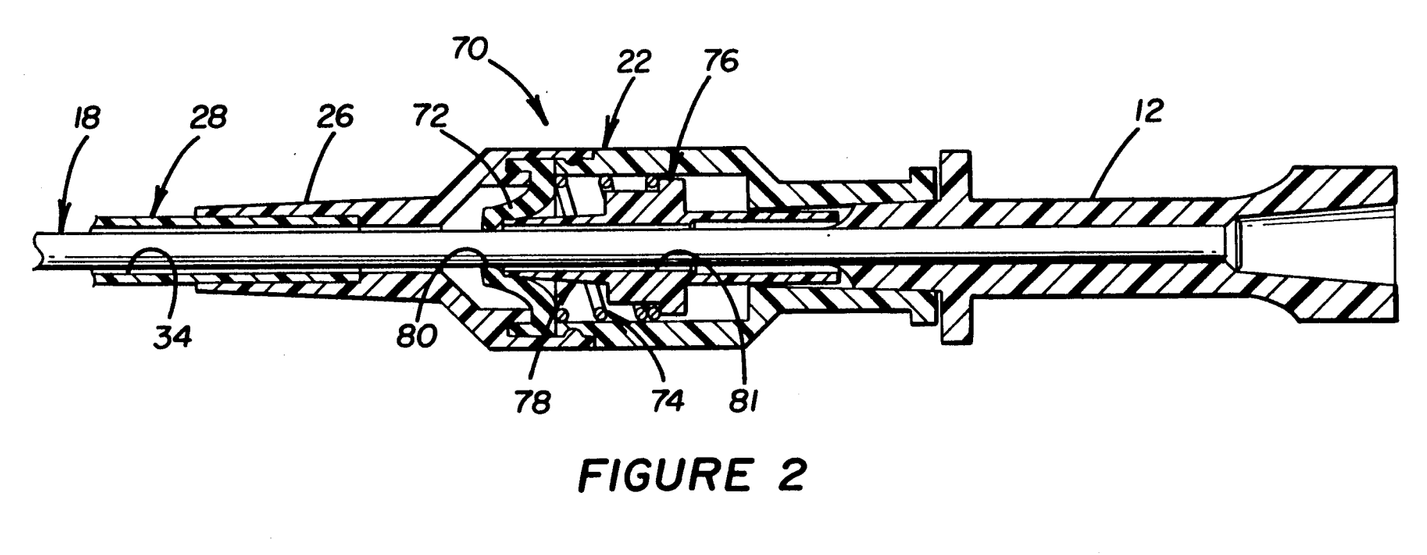
FIG. 2 illustrates, in side elevational sectioned view, the assembly of FIG. 1.

The present invention provides a multi-lumen catheter assembly 10 (FIG. 5) which can be inserted using an over-the-needle technique, as illustrated in, for example, FIGS. 1-4. Referring to FIG. 1, the insertion assembly 11 includes a needle hub 12 having a proximal end portion 14 and a distal end portion 16. A needle 18 is attached to extend distally from the needle hub distal end portion 16.

In FIG. 1 an outer cannula hub 22 is shown which has a proximal end portion 24 and a distal end portion 26. The distal end portion 16 of the needle hub 12 fits within the proximal end portion 24 of the outer cannula hub 22. An outer cannula 28, which has a proximal end portion 30 and a distal end portion 32, has its proximal end portion 30 attached to an outer cannula attachment region 31. The outer cannula 28 extends from the distal end portion 26 of the outer cannula hub 22. The needle 18 fits through an internal lumen 34 (FIG. 2) of the outer cannula 28 and extends beyond the distal end portion 32 of the outer cannula 28. Suitably the needle 18 will fit snugly but slidingly within the inner lumen 34 of the outer cannula 28. For ease and clarity of illustration the needle 18 and the internal lumen 34 are illustrated as having a somewhat larger gap between them.

In accordance with the invention an insertion assembly 11 as illustrated in FIG. 1 is inserted a desired distance into a selected blood vessel, normally a vein, after which the needle hub 12 is withdrawn leaving behind the outer cannula hub 22 and the attached outer cannula 28. In a manner which will be discussed below, blood flow is but off at the outer cannula hub 22 so that no significant bleeding results.

Figure 3:
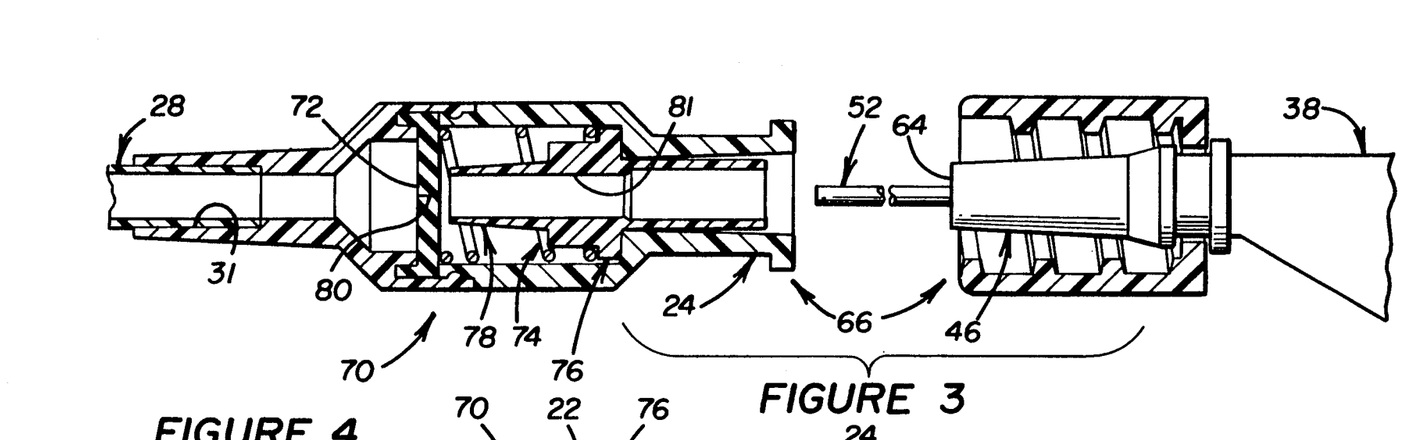
FIG. 3 illustrates, in side elevational sectioned view, a catheter assembly in accordance with an embodiment of the present invention positioned for assembly.
Figures 4, 5:
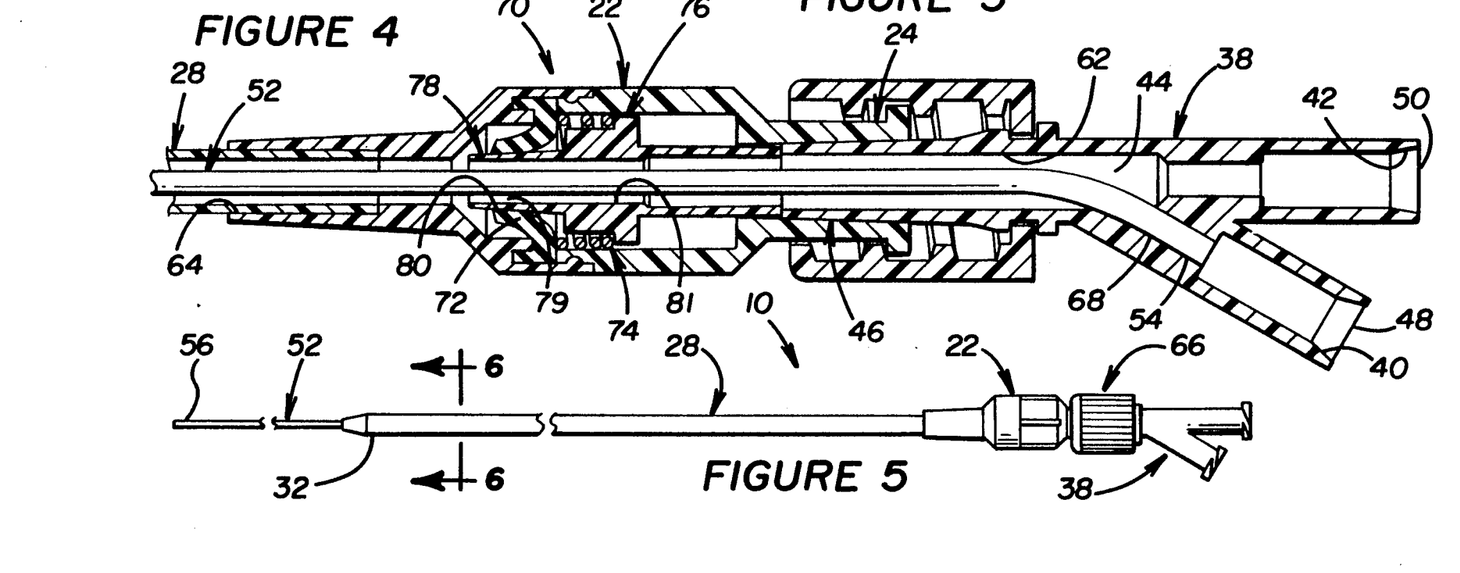
FIG. 4 illustrates, in sectional view similar to FIG. 3 but following assembly, the embodiment of the present invention also illustrated in FIG. 3.
FIG. 5 illustrates, in side elevational view, the catheter assembly of FIG. 4.

FIGS. 3 and 4 illustrate an inner lumen positioning assembly 38. The positioning assembly 38 is in the nature of an inner cannula hub having a first internal passage 40 and a second internal passage 42 which join one another at a junction region 44. The inner cannula hub 38, in the embodiment illustrated having a Y-shape, includes a distal end region 46. A first proximal access region 48 provides access to the first passage 40. A second proximal access region 50 provides access to the second passage 42. An inner cannula 52 has a proximal end region 54 and a distal end region 56 (FIG. 5). The proximal end region 54 of the inner cannula 52 is attached with its inner lumen 58 (FIG. 6) in flow communication with the first internal passage 40 of the inner cannula hub 38 but free from communication with the second internal passage 42 of the inner cannula hub 38.

FIGS. 4 and 5 illustrate a multi-lumen catheter assembly 10 (in inserted form) in accordance with an embodiment of the present invention. It is produced by inserting the assembly 11 of FIG. 1 in a blood vessel, withdrawing the needle 18 and needle hub 12 and inserting the positioning assembly 38 of FIG. 3. The inner cannula 52 is positioned within the outer cannula 28 (FIGS. 3 and 4). The distal end portion 56 of the inner cannula 52, in the embodiment illustrated, extends beyond the distal end portion 32 of the outer cannula 28. In this manner non-compatible medicaments can be introduced into a blood vessel or other body cavity a spaced distance apart from one another. Or, samples can be removed from a region of the vessel or cavity which is free of a particular medicament which is being introduced via another lumen.

Figure 6:
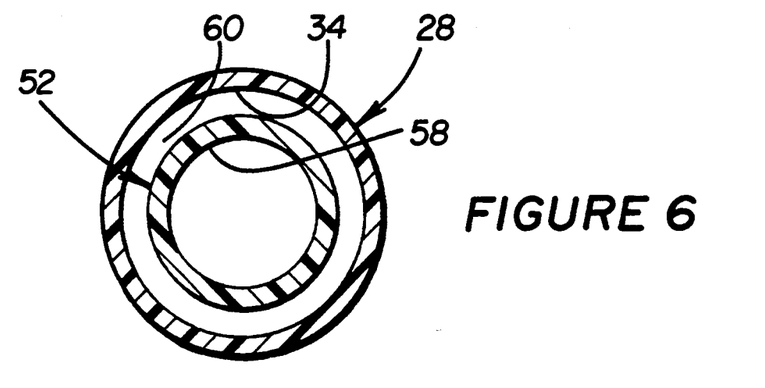
FIG. 6 illustrates a view taken along the line 6—6 of FIG. 5.

FIG. 6 illustrates the fact that an annular passage 60 between the outer cannula 28 and the inner cannula 52, which is the remaining available portion of the outer cannula lumen 34, can serve as a passage for introducing or extracting fluid from a blood vessel. In addition, the inner lumen 58 can be used for this purpose. The inner lumen 58 and the passage 60 can alternatively be used for introduction and/or extraction of sensors, surgical apparatus, fiber optics, etc.

As may be seen in FIGS. 3 and 4 the junction region 44 serves to form an exit passage 62 to which access is provided by an exit passage access region 64. The distal end region 46 of the inner cannula hub 38 may be seen to be connectable to the proximal end portion 24 of the outer cannula hub 22, for example utilizing a Luer locking mechanism 66 to accomplish the connection. Other connecting mechanisms can also be used including a simple siding fit. As will also be noted an inner cannula attachment region 68 is provided which is adapted to be connected to the proximal end portion 54 of the inner cannula 52, for example by a press fit or plastic welding technique. This connection is upstream of the junction 44 whereby the lumen 58 of the inner cannula 52 is not in flow communication with the second internal passage 42 of the inner cannula hub 38.

FIGS. 3 and 4 also illustrate the outer cannula tub 22 and valve means 70 which can be associated with the outer cannula hub 22 and which serves for normally closing communication between the second passage 42 of the inner cannula hub 38 and the outer cannula lumen 34. The valve means 70 is openable sufficiently for the inner cannula 52 to pass through it. When the valve means 70 is open it also opens up flow communication between the second passage 42 and the outer cannula lumen 34, the flow communication being accomplished in a manner which is described immediately below.

The particular valve means 70 illustrated includes a self-sealing septum 72, a spring 74 and a shuttle 76 which includes a tubular portion 78 which on compression of the spring 74 extends through a self-sealing opening 80 in the self-sealing septum 72. The tubular portion 78 has an inner diameter 81 sufficiently large so that the inner cannula 52 can pass through it and can leave an annular space 79, of generally about the size of the annular passage 60, open between the inner cannula 52 and the tubular portion 78. It is through the annular space 79 that flow communication is provided between the second passage 42 and the outer cannula lumen 34.

Operation of the valve means 72 is apparent from comparison of FIGS. 3 and 4. In FIG. 3 the distal end region 46 of the inner cannula hub 38 has not been slid within the proximal end portion 24 of the outer cannula hub 22. Once this occurs, as seen in FIG. 4, the tubular portion 78 will have been forces through the self-sealing opening 80 in the self-sealing septum 72 thereby both opening the annular space and preventing pressure from being applied by the septum 72 to the inner cannula 52 which might cause it to be shut off. This allows the insertion of a relatively soft inner cannula 52 or of an inner cannula 52 which softens on being inserted in a blood vessel. It should be noted that in the embodiment illustrated in FIGS. 3 and 4 the inner cannula 52 passes through the self-sealing opening 80 in the self-sealing septum 72 before the shuttle 76 is moved so as to force the tubular portion 78 therethrough. Thus, the inner cannula 52 should have sufficient stiffness, at least when initially inserted, so as to be able to be forced through the self-sealing opening 80. It should be noted that the valve means 70 provides a virtually bloodless manner for changing intravenous connection. Furthermore, it eliminates the need for clamping or kinking tubing during such exchanges. Still further, the chances of air emboli or bleeding due to accidental disconnection of an IV (intravenous) set is significantly reduced. Moreover, infusion and aspiration can be carried out rather than only one or the other. Yet further, the apparatus as illustrated accepts standard luers and fits in standard luers.

It is also important to understand that flow from the second passage 42 into the outer cannula lumen 34 washes through and cleanses the valve means 70 thereby eliminating any dead space which would be present if the flow into the outer cannula lumen 34 was introduced downstream of the valve means 70.

While the inner cannula hub 38 is illustrated as opening the valve means 70 in FIGS. 3 and 4, it should be recognized that the inner cannula hub 38 is merely illustrative of one type of access member which can provide access through the valve means 70. It may be desirable to open the valve means 70 for other reasons. For example, it may be desirable to insert a radiopaque wire through the valve means 70 so as to be able to measure the length of cannula which will be needed to reach a particular portion in a blood vessel. Accordingly, the invention includes such a mechanism and method.

Figures 7, 10, 12:
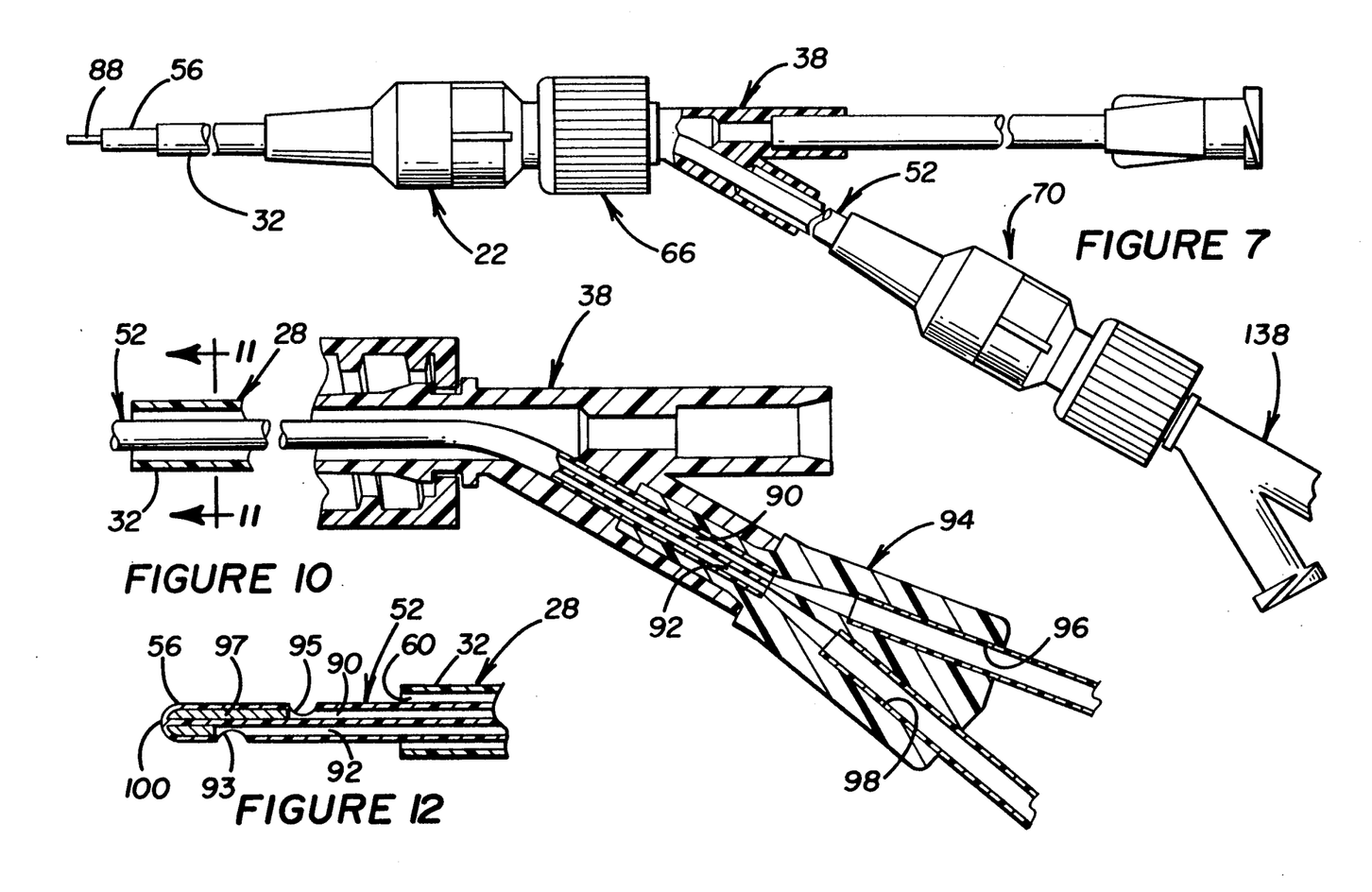
FIG. 7 illustrates, in partially sectioned partial side sectional view, a catheter assembly in accordance with an alternate embodiment of the present invention.
FIG. 10 illustrates, in side elevational sectioned view, a catheter assembly in accordance with another alternate embodiment of the present invention.
FIG. 12 illustrates, in partial elevational view, a detail in the distal portions of an inner cannula and an outer cannula in accordance with an embodiment of the present invention.
Figure 8:
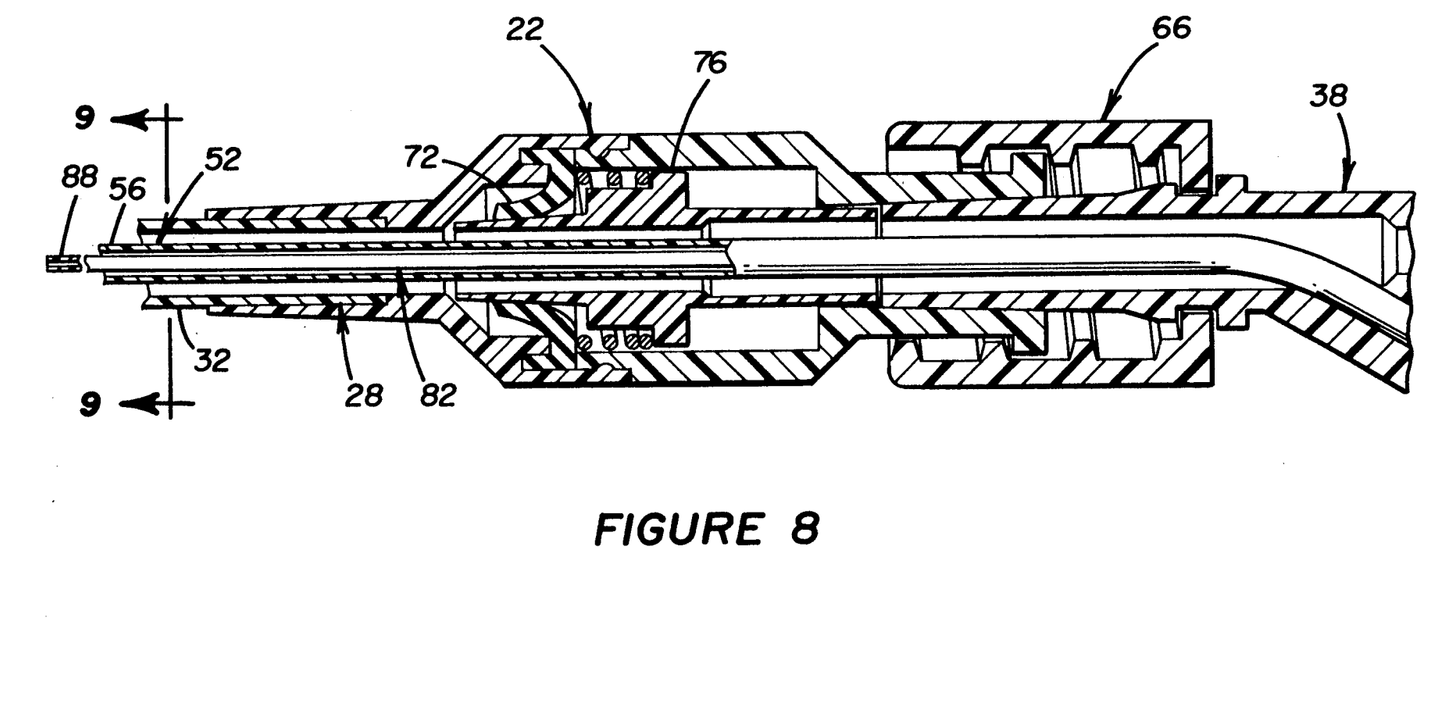
FIG. 8 illustrates, in a view similar to FIG. 4, a catheter assembly in accordance with FIG. 7.
Figure 9:
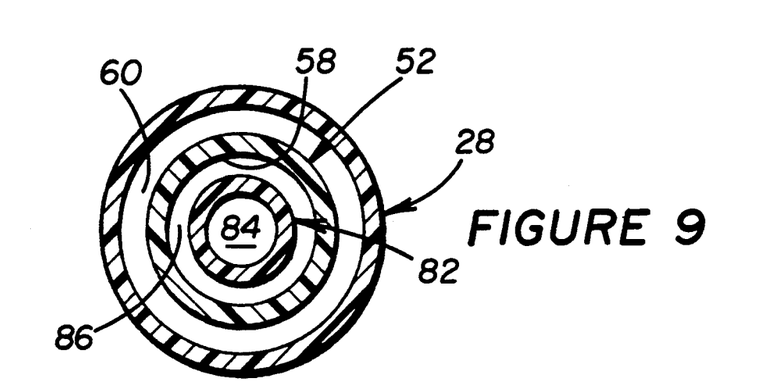
FIG. 9 illustrates, in a view similar to FIG. 6, the catheter assembly of FIG. 7.

FIGS. 7, 8 and 9 illustrate an embodiment of the present invention wherein, in addition to the previously mentioned outer cannula 28 and inner cannula 42, a further inner cannula 82 is present within the lumen 58 of the inner cannula 52. The further inner catheter 82 has its own further inner lumen 84. Between the inner cannula 52 and the further inner cannula 82, a passage 86 exists through which fluids, etc., can be introduced or withdrawn. Thus, the configuration of FIGS. 7-9 provides for the introduction or extraction of three fluids, etc., one through the passage 60, one through the passage 86 and one through the lumen 84. And, the respective distal end portions 88 of the further inner cannula 82, 56 of the inner cannula 52 and 32 of the outer cannula 28 can have openings which are spaced apart from one another whereby medicaments, etc., can be inserted and/or samples can be withdrawn and/or nutrient solution can be inserted at spaced distances apart from one another for reasons which have been discussed previously. In the embodiment of FIGS. 7-9 the inner cannula 52 has been attached to the inner cannula hub 38 in the manner shown in FIG. 4 and an additional inner cannula hub 138 has been added which includes its own valve means 70 which can be of the nature shown in FIGS. 3 and 4, through which the further inner catheter 82 can be inserted. It will be obvious that this type of concentric insertion can be continued to the extend desired and the only limiting factor is the size of the outer cannula 28 which may be inserted in the patient's blood vessel. FIG. 8 illustrates the resulting assembly.

Figure 11:
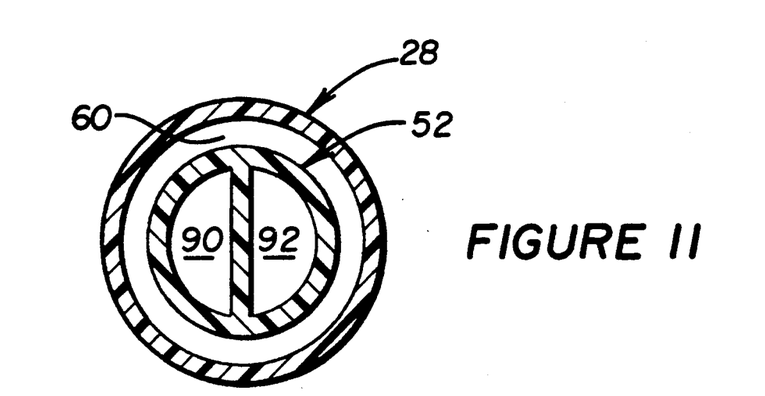
FIG. 11 illustrates, in a view similar to FIG. 6, the catheter assembly of FIG. 10.

FIGS. 10-12 illustrate an embodiment of the present invention much like that of FIGS. 1-6, but wherein the inner cannula 52 is divided into two lumens, 90 and 92 thereby providing three different passages, namely the passage 60 and the lumens 90 and 92, for introduction and extraction of fluids, etc., from a blood vessel. As can be seen in FIG. 12 the distal end portion 56 of the inner cannula 52 can advantageously made to be blunt ended. One advantage is that when the distal end portion 56 is blunt ended (and generally smooth) the intima of the blood vessel is less likely to be damaged during insertion of the inner cannula 52 as compared with inserting an open ended cannula. Also, if desired a radiopaque member 97, generally a piece of metal or material loaded with radiopaque filler, may be encased in a distal end 100 of the inner lumen 52 (in lumen 90 and/or lumen 92), the radiopaque member 97 serving to provide a marker which allows location of catheter assembly 10 at a desired position within a blood vessel.

In the embodiment shown in FIG. 12 the lumen 92 opens at lateral opening 93 located farther distally along the distal end portion 56 of the inner cannula 52 than does the lumen 90 which opens at lateral opening 95. Also, the opening to passage 60 is at the end of the distal portion 32 of the outer cannula 28 and is a spaced distance proximally from the opening 95. In this manner spaced apart introduction and/or extraction of fluids, etc., is provided.

In the embodiment of FIGS. 10-12 it is not necessary to have an additional valve means 70. Instead, an additional inner cannula hub 94 is provided having a first internal passage 96 communicating with the lumen 90 and having a second internal passage 98 communicating with the lumen 92. It should be noted that while the passage 90 and 92 are shown to be each substantially semicircular in shape any other desired shape can be utilized. Or, separate tubes can be provided within the inner cannula 52, each having a different exit. Spaced apart introduction and/or extraction of fluids, etc., is provided as with the other embodiments of the invention. An additional valve means 70 is not required.

As has been alluded to it is advantageous if the outer cannula 28 is formed of a material which softens and which swells to increase both its size and the size of its lumen 34 on being inserted into a blood vessel. Generally, it is preferred that the outer cannula 28 softens by a factor (2.4% Secant Modulus ratio) of at least about 2:1, preferably at least about 3;1, upon insertion. There are also advantages in having the inner cannula 52 soften by a like amount upon insertion. Alternatively, the inner cannula 52 can simply be formulated of a soft material to begin with. This serves to further reduce irritation to the intima of a blood vessel. Also, the outer cannula 28 preferably is fabricated from a material that swells in volume by a factor of at least about 1.3:1 on being inserted in a blood vessel. This provides the advantage of allowing the use a smaller needle 18 to insert a cannula of a desired and significantly larger size making possible over-the-needle insertion of multi-lumen catheters. The inner cannula 52 can also swell so long as it does not swell enough to block off flow through the outer cannula lumen 34 or through the tubular member 78.

In the case of cannula which soften on being inserted in a blood vessel it may be desirable to provide coatings on such cannula where they pass through the patient's tissue near the vein wall so as to prevent any kinking from occurring.

In a preferred embodiment, the catheter assembly comprises a cannula of a desired or adjustable length with outer and inner circumferences which increase and/or of a material whose 2.5% Secant Modulus decreases when inserted in a patient.

the cannulae (inner and outer) of the invention can be of any material suitable for introduction into a living subject. Preferably, these materials are polymeric in nature and are selected to be sufficiently stiff for insertion. In general, the cannulae should, when inserted have a 2.5% Secant Modulus greater than about 20,000 N/cm$^2$ and preferably greater than about 28,000 N/cm$^2$ to prevent buckling or wrinkling upon insertion into the subject. Even more preferred are those compositions which soften or exhibit a decreased 2.5% Secant Modulus upon, for example, exposure to liquids, insertion of the distal end portion of the cannula into the body of a living subject and its maintenance therein, or exposure to a temperature from about 20° C. to about 40° C. Particularly, preferred compositions absorb liquid (i.e., hydrate) and thereafter soften to a 2.5% Secant Modulus of less than 7,000 N/cm$^2$ which reduces the trauma to the surrounding tissues of the subject. The inner cannula can simply have a 2.5% Secant Modulus of less than 7,000 N/cm² to begin with. The term softening ratio is used herein to refer to the ratio of the 2.5% Secant Modulus values of the composition selected in the form of a tubular cannula initially to the 2.5% Secant Modulus of the composition when softened. It is preferred that at least a portion of such compositions are hydrophilic. It is also preferred that the composition soften when a softening ratio of at least about 2:1.

Examples of softening polymers useful in the practice of the invention are those described in U.S. Pat. Nos. 4,883,699, issued Nov. 28, 1987 and 4,911,691, issued Mar. 27, 1990, both of which are incorporated herein by reference. The preferred composition for the cannula comprises:

(a) a first phase which comprises a substantially non-hydrophilic polymeric component; and (b) a second phase which comprises a hydrophilic polymeric component;

the material (i) being capable of absorbing water to an extent that its softens with a softening ratio of at least about 2:1 and/or swells with a swelling ratio of at least about 1.3:1; and (ii) when substantially completely hydrated, having an energy to break of at least about 700 N-cm/cm³ and a 2.5% Secant Modulus of less than about 7,000 N/cm².

Also useful are those softening polymers described in U.S. Pat. Nos. 4,359,558; 4,424,305; 4,454,309 and 4,439,583 of Tyndale Plains-Hunter Ltd. incorporated herein by reference. The preferred cannula composition essentially comprises a polyurethane diacrylate composition having from about 90 to about 65 weight percent of a hydrophilic polyurethane resin and from about 10 to about 35 weight percent of a diacrylate.

An alternative material which may be utilized as a cannula material is a thermoplastic composition with softenable and/or shaped-memory properties. Such polymeric compositions are described, for example, in the following articles: Softenable, Shape-Memory Thermoplastics for Biomedical Use, Robert S. Ward, M.D. 7 D, August 1975; and Thrombroresistant, Radiopaque, Softenable Thermoplastics Catheter Compounds With Shape-Memory Properties, R. S. Ward, K. A. White, J. S. Riffle, Second World Congress On Biomaterials, 10th Annual Meeting of the Society For Biomaterials, Washington, D.C., Apr. 27,–May 1, 1984. The aforementioned thermoplastic compositions comprise a base polymer that is a block or segmented copolymer thermoplastic with at least one block type with an abrupt effective glass transition temperature ($T_g$) at or greater than room temperature, but less than approximately body temperature. The remainder of the base polymer contains hard blocks whose dominant thermal transition is substantially greater than body temperature. The cannulae can also be made to expand and soften as follows. The cannulae are originally made with their eventually desired expanded internal diameter and then are heated above the glass transition temperature ($T_g$), drawn out to form longer and thinner cannulae and held in this state until cooled below the glass transition temperature. Once the longer and thinner cannulae have warmed to a temperature that is greater than room temperature but less than approximately body temperature, i.e., once the cannulae have reached the glass transition temperature, the shape-memory properties operate and the cannulae increase in internal and external diameter while shrinking in length.

It is also preferred when selecting such softening materials of the cannulae that such materials also swell wherein at least a portion of the cannula inner cross-section of the duct and/or outer circumference of the cannula increases to form an enlarged inner cross-section of the duct and/or enlarged outer circumference of the cannula when inserted in a living subject and maintained therein and/or when the duct is contacted by a liquid for a period of time sufficient for the enlarged duct cross-section and/or outer circumference to form. Preferably, the duct cross-section increases from about 25% to about 400%.

The composition of the cannula may be cross-linked if desired. Cross-linking give the composition strength wherein the melting or softening points of the uncross-linked polymeric components permit sterilization of the catheter assembly using a cannula of such composition at above such temperature. Cross-linking of the material selected for the cannula may also be used to adjust the 2.5% Secant Modulus of the composition to a desired value. Cross-linking may also increase the tensile energy to break of the material which has been softened. Cross-linking can also be used to minimize extractable components of the composition.

Cross-linking can be effected by use of an appropriate cross-linking agent or by radiation, preferably in the presence of a cross-linking promoter, such as triallyl isocyanourate or the like. Or, the material can be cross-linked by high energy gamma or beta radiation.

The material of the cannulae may contain additional ingredients such as stabilizers, antioxidants, radiopacifiers, medicaments, fillers or the like. For certain applications it may be advantageous to incorporate a water soluble or water dispersable medicament which can leach from the material when it contacts the fluids of the living subject. Such medicaments include anti-thrombogenic agents, antibiotics, antimicrobial, antiviral agents, anticoagulants, anti-inflammatory agents, and the like.

A cannulae selected such that it swells or softens should not do so appreciable during the time it is being inserted in a living subject or the like. It is preferable that such cannulae's swelling or softening time should be at least about 15 seconds and preferably at least about 60 seconds.

The swelling of the cannula has several advantages. Swelling of the cannula permits insertion of a smaller device for equivalent fluid flow and/or can result in pressure around a wound site reducing bleeding and bacterial invasion into the wound and prevent catheter slip out, a common cause for changing catheters prematurely. Increased cross-section of the cannula duct also permits increased flow through the cannula and/or the positioning of a larger inner cannula when compared with similar non-swelling cannula of identical initial dimensions. This allows access to smaller areas such as the veins in the limbs and easier insertion into the selected site. Further, if the cannula is fed into the blood vessel using an inserter having a channel through which the cannula is fed, swelling of the cannula may increase the outer circumference sufficiently that it becomes as great as the diameter of the inserted channel. After insertion of the cannula this may be desirable. The inserter then looses its ability to slide relative to the cannula due to the pressure of the cannula against the inserter channel. This is advantageous in preventing relative movement of the cannula and inserter. Once the inserter is attached (e.g., by taping) to the subject, further movement of the cannula in or out of the subject is limited. Cannulae which becomes soft are also advantageous. A soft cannula tends to cause less irritation to the intima (lining of the vein) and to the insertion site and is less likely to contribute to mechanical phlebitis. The softness of the cannula also permits it to float in a vein rather than lie on the point where inserted and consequently any infusion is delivered evenly helping to avert chemical phlebitis.

Industrial Applicability

The present invention provides an over-the-needle multi-lumen catheter assembly 10 which is particularly useful for inserting multi-lumen cannula into veins such as the superior vena cava.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

The which is claimed is:

1. An over-the-needle insertable multi-lumen catheter assembly, comprising:
   an attachment structure have proximal and distal end regions, first and second internal passages which join one another at a junction region to form a distal exit passage, an outer cannula attachment region of a size and construction sufficient to allow a needle to be inserted therethrough, an inner cannula attachment region, a first proximal access region providing access to the first passage, a second proximal access region providing access to the second passage and an exit passage access region providing access to the distal exit passage;
   an outer cannula having proximal and distal end portions and an outer cannula lumen, the proximal end portion of the outer cannula being attached to the outer cannula attachment region, the outer cannula lumen being of a size sufficient to allow the needle to be inserted therethrough;
   an inner cannula having proximal and distal end portions and an inner cannula lumen, the proximal end portion of the inner cannula being attached to the inner cannula attachment region in such a manner that fluid flow communication is blocked between the first proximal access region and the outer cannula lumen, the inner cannula being insertable axially through the first passage and the outer cannula lumen, the inner cannula being of a construction such that when inserted in to the outer cannula lumen it does not prevent flow therethrough; and
   valve means associated with the attachment structure for closing communication between the second passage and the outer cannula lumen, the valve means being openable sufficiently for the inner cannula to pass therethrough and to open up communication between the second passage and the outer cannula lumen.

2. An assembly as set forth in claim 1, wherein the outer cannula softens by at least a ratio of 2:1 on being inserted in a blood vessel.

3. An assembly as set for in claim 2, wherein the valve means comprises a septum having a self-sealing opening therethrough.

4. An assembly as set forth in claim 3, wherein the valve means further includes:
   a rigid sleeve having an internal diameter sufficient to allow the inner cannula to pass therethrough leaving a surrounding annular space through which a fluid can flow; and
   means for positioning the sleeve through the self-sealing opening.

5. An assembly as set forth in claim 2, wherein the outer cannula lumen swells by at least 1.3:1 on the outer cannula being inserted in a blood vessel.

6. An assembly as set forth in claim 5, wherein the valve means comprises a septum having a self-sealing opening therethrough.

7. An assembly as set forth in claim 6, wherein the valve means further includes:
   a rigid sleeve having an internal diameter sufficient to allow the inner cannula to pass therethrough leasing a surrounding annular space through which a fluid can flow; and
   means for positioning the sleeve through the self-sealing opening.

8. An assembly as set forth in claim 1, wherein the outer cannula lumen swells by at least 1.3:1 on the outer cannula being inserted in a blood vessel.

9. An assembly as set forth in claim 1, wherein the valve means comprises a septum having a self-sealing opening therethrough.

10. An assembly as set forth in claim 9, wherein the valve means further includes:
    a rigid sleeve having an internal diameter sufficient to allow the inner cannula to pass therethrough leaving a surrounding annular space through which a fluid can flow; and
    means for positioning the sleeve through the self-sealing opening.

11. An assembly as set forth in claim 10, wherein the valve means comprises a septum having a self-sealing opening therethrough.

12. An assembly as set forth in claim 11, wherein the attachment structure further includes a rigid sleeve having an internal diameter sufficient to allow the inner cannula to pass therethrough and means for positioning the sleeve through the self-sealing opening.

13. An assembly as set forth in claim 1, wherein the attachment structure includes:
    an outer cannula hub having a proximal end portion and the attachment structure distal end portion and including the outer cannula attachment region and a distal portion of the exit passage access region; and
    an inner cannula hub having a distal end portion, the attachment structure proximal end portion, the first and second internal passages, the junction region, the distal exit passage, the inner cannula attachment region, the first proximal access region, the second proximal access region and a proximal portion of the exit passage access region;
    the distal end portion of the inner cannula hub being releasably couplable to the proximal end portion of the outer cannula hub with the distal and proximal portions of the exit passage access region in flow communication.

14. An assembly as set forth in claim 13, further including:
    a further inner cannula hub having further inner cannula hub distal and proximal end portions, first and second further inner cannula hub internal passages, a junction region defined by the joining of the first and second internal passages, a distal exit passage, a further inner cannula attachment region, a first proximal further access region, a second proximal further access region and an exit passage access region, the distal end portion of the further inner cannula hub being releasably couplable to the proximal end portion of the inner cannula hub with the exit passage access regions of the inner cannula hub and of the further inner cannula hub in flow communication;

a further inner cannula having proximal and distal end portions and a further inner cannula lumen, the proximal end portion of the further inner cannula being attached to the further inner cannula attachment region in such a manner that fluid flow communication is blocked between the first proximal further access region and the inner cannula lumen, the further inner cannula being insertable axially through the first passage of the further inner cannula hub and the inner cannula lumen, the further inner cannula being of a construction such that when inserted into the inner cannula lumen it does not prevent flow therethrough; and further valve means associated with the inner cannula hub for closing communication between the further inner cannula second passage and the inner cannula lumen, the further valve means being openable sufficiently for the further inner cannula to pass therethrough and to open up communication between the further inner cannula second passage and the inner cannula lumen.

15. An assembly as set forth in claim 14, wherein the first mentioned valve means comprises a septum having a self-sealing opening therethrough.

16. An assembly as set forth in claim 15, wherein the first mentioned valve means further includes:
a rigid sleeve having an internal diameter sufficient to allow the inner cannula to pass therethrough leaving a surrounding annular space through which a fluid can flow; and
means for positioning the sleeve through the self-sealing opening.

17. An assembly as set forth in claim 1, wherein said inner cannula is internally divided into a plurality of internal lumens, and wherein said assembly further includes:
a plurality of inner lumen access passages each of which provides access to a respective one of said plurality of internal lumens.

18. An assembly as set for in claim 17, wherein the valve means comprises a septum having a self-sealing opening therethrough.

19. An assembly as set forth in claim 18, wherein the valve means further includes:
a rigid sleeve having an internal diameter sufficient to allow the inner cannula to pass therethrough leaving a surrounding annular space through which a fluid can flow; and
means for positioning the sleeve through the self-sealing opening.

20. A catheter structure with which the number of available lumens can be changed without removal from a patient's body, comprising:
an outer cannula hub having proximal and distal end portions, a passageway therethrough from the distal to the proximal end portion thereof and an outer cannula attachment region;

an inner cannula hub having proximal and distal end portions, a first internal passage therethrough from the distal to the proximal end portion thereof and a second internal passage which joins the first internal passage at a junction region, an inner cannula attachment region, the distal end portion of the inner cannula hub being releasably couplable to the proximal end portion of the outer cannula hub with the first internal passage in the inner cannula hub in communication with the passageway through the outer cannula hub;

an outer cannula having proximal and distal end portions and an outer cannula lumen, the proximal end portion fo the outer cannula being attached to the outer cannula attachment region so that the outer cannula extends distally from the outer cannula hub;

an inner cannula attached to the inner cannula attachment region in such a manner as to block fluid flow communication between the proximal and distal end portions of the first passage, the inner cannula having proximal and distal end portions, the distal end portion thereof being insertable through the passageway in the outer cannula hub from the proximal end portion thereof and out of the distal end portion thereof; and an elastomeric septum having a self-sealing opening therethrough associated with the outer cannula hub for closing communication between the second passage and the outer cannula lumen, the distal end portion of the inner cannula being insertable through the opening through the septum; and inner cannula sheathing means for preventing the septum from exerting inward radial pressure on the inner cannula when the inner cannula distal end portion is inserted through the opening in the septum and for providing fluid flow communication of the second passage with the outer cannula lumen.

21. A catheter structure as set forth in claim 20, wherein the outer cannula softens by at least a ratio of 2:1 on being inserted in a blood vessel.

22. A catheter structure as set forth in claim 21, wherein the inner cannula softens by at least a ratio of 2:1 on being inserted in a blood vessel.

23. A catheter structure as set forth in claim 22, wherein the inner cannula sheathing means comprises:
a rigid sleeve having an internal diameter sufficient to allow the inner cannula to pass therethrough and sufficient to allow fluid to flow between the inner cannula and the sleeve; and
means for positioning the sleeve through the self-sealing opening.

24. A catheter structure as set forth in claim 22, wherein the outer cannula lumen swells by at least 1.3:1 on the outer cannula being inserted in a blood vessel.

25. A catheter structure as set forth in claim 21, wherein the inner cannula sheathing means comprises:
a rigid sleeve having an internal diameter sufficient to allow the inner cannula to pass therethrough and sufficient to allow fluid to flow between the inner cannula and the sleeve; and
means for positioning the sleeve through the self-sealing opening.

26. A catheter structure as set forth in claim 21, wherein the outer cannula lumen swells by at least 1.3:1 on the outer cannula being inserted in a blood vessel.

27. A catheter structure as set forth in claim 21, wherein the inner cannula softens by at least a ratio of 2:1 on being inserted in a blood vessel.

28. A catheter structure as set forth in claim 27, wherein the inner cannula sheathing means comprises:
   a rigid sleeve having an internal diameter sufficient to allow the inner cannula to pass therethrough and sufficient to allow fluid to flow between the inner cannula and the sleeve; and
   means for positioning the sleeve through the self-sealing opening.

29. A catheter structure as set forth in claim 28, wherein the outer cannula lumen swells by at least 1.3:1 on the outer cannula being inserted in a blood vessel.

30. A catheter structure as set forth in claim 21, wherein the inner cannula, when softening on being inserted in a blood vessel, exhibits a 2.5% Secant Modulus of no more than 7,000 N/cm$^2$.

31. A catheter structure as set forth in claim 21, wherein the inner cannula exhibits a 2.5% Secant Modulus of no more than 7,000 N/cm$^2$.

32. A catheter structure as set forth in claim 31, wherein the inner cannula sheathing means comprises:
   a rigid sleeve having an internal diameter sufficient to allow the inner cannula to pass therethrough and sufficient to allow fluid to flow between the inner cannula and the sleeve; and
   means for positioning the sleeve through the self-sealing opening.

33. A catheter structure, comprising:
   an attachment structure having proximal and distal end regions, first and second internal passages which join one another at a junction region to form a distal exit passage, an outer cannula attachment region, an inner cannula attachment region, a first proximal access region providing access to the first passage, a second proximal access region providing access to the second passage and an exit passage access region providing access to the distal exit passage;
   an outer cannula having proximal and distal end portions and an outer cannula lumen and being formulated of a material that softens with a softening ratio of greater than 2:1, the proximal end portion of the outer cannula being attached to the outer cannula attachment region;
   an inner cannula having proximal and distal end portions and an inner cannula lumen, the proximal end portion of the inner cannula being attached to the inner cannula attachment region in such a manner as to block fluid flow communication between the proximal and distal end portions of the first passage, the inner cannula being insertable axially through the first proximal access region and the first passage; and
   valve means associated with the attachment structure for closing communication between the second passage and the outer cannula lumen, the valve means being openable sufficiently for the distal end portion of the inner cannula to pass therethrough and to open communication between the second passage and the outer cannula lumen.

34. A catheter structure as set forth in claim 33, further including:
   inner cannula sheathing means for preventing the valve means from exerting inward radial pressure on the inner cannula when the inner cannula is inserted through the valve means.

35. A catheter structure as set forth in claim 34, wherein the valve means comprises a septum having a self-sealing opening therethrough.

36. A catheter structure as set forth in claim 35, wherein the inner cannula sheathing means comprises:
   a rigid sleeve having an internal diameter sufficient to allow the inner cannula to pass therethrough; and further including:
   means for positioning the sleeve through the self-sealing opening.

37. A catheter structure as set forth in claim 34, wherein the outer cannula lumen swells by at least 1.3:1 on the outer cannula being inserted in a blood vessel.

38. A catheter structure as set forth in claim 37, wherein the inner cannula sheathing means comprises:
   a rigid sleeve having an internal diameter sufficient to allow the inner cannula to pass therethrough; and further including:
   means for positioning the sleeve through the valve means.

39. A catheter assembly as set forth in claim 33, wherein said inner cannula is formulated of a material that softens with a softening ratio of greater than 2:1.

40. A catheter assembly, comprising:
   an outer cannula hub having proximal and distal end portions and defining a central longitudinal passageway therethrough having proximal and distal end portions, the passageway extending from the outer cannula hub proximal end portion to the outer cannula hub distal end portion;
   an outer cannula having proximal and distal end portions and defining an outer cannula lumen extending from the outer cannula proximal end portion to the outer cannula distal end portion, the outer cannula proximal end portion being attached to the outer cannula hub with the outer cannula lumen in flow communication with the outer cannula hub passageway;
   an inner cannula hub having proximal and distal end portions and defining first and second passageways therethrough;
   an inner cannula having proximal and distal end portions and defining an inner cannula lumen extending from the inner cannula proximal end portion to the inner cannula distal end portion, the inner cannula proximal end portion being attached to the inner cannula hub with the inner cannula lumen in flow communication with the inner cannula hub first passageway and such that fluid flow from the inner cannula hub first passageway can only proceed through the inner cannula lumen;
   attaching means for detachably attaching the inner cannula hub to the outer cannula hub with the inner cannula positioned within and extending longitudinally along the outer cannula lumen; and
   valve means associated with the outer cannula hub for blocking communication between the proximal end portion of the outer cannula hub passageway and the outer cannula lumen, the valve means being openable in response to the inner cannula hub being attached to the outer cannula hub, the valve means, when open, providing flow therethrough from the inner cannula hub second passageway to the outer cannula lumen.

41. A catheter assembly as set forth in claim 40, further including:
   an outer cannula lumen access member having proximal and distal end portions and an access member passageway therethrough, the access member being detachably attachable to the outer cannula hub by the attaching means if the inner cannula hub is not so attached, the valve means opening in response to attachment of the access member to the outer cannula hub, the valve means, when open, providing flow therethrough from the access member passageway to the outer cannula lumen.

42. A catheter structure as set forth in claim 41, wherein the valve means comprises a septum having a self-sealing opening therethrough;

- a rigid sleeve having an internal diameter sufficient to allow the inner cannula to pass therethrough with sufficient clearance to allow fluid flow from the inner cannula second passageway to the outer cannula lumen; and
- means for positioning the sleeve through the self-sealing opening.

43. A catheter structure as set forth in claim 40, wherein the valve means comprises a septum having a self-sealing opening therethrough;

- a rigid sleeve having an internal diameter sufficient to allow the inner cannula to pass therethrough with sufficient clearance to allow fluid flow form the inner cannula second passageway to the outer cannula lumen; and
- means for positioning the sleeve through the seal-sealing opening.

44. A catheter structure with which the number of available lumens can be changed without removal from a patient's body, comprising:

- an outer cannula hub having proximal and distal end portions, a passageway therethrough from the distal to the proximal end portion thereof and an outer cannula attachment region;
- an inner cannula hub having proximal and distal end portion, a first internal passage therethrough from the distal to the proximal end portion thereof and a second internal passage which joins the first internal passage at a junction region, an inner cannula attachment region, the distal end portion of the inner cannula hub being releasably couplable to the proximal end portion of the outer cannula hub with the first internal passage in the inner cannula hub in communication with the passageway through the outer cannula hub;
- an outer cannula having proximal and distal end portions and an outer cannula lumen, the proximal end portion of the outer cannula being attached to the outer cannula attachment region so that the outer cannula extends distally from the outer cannula hub;
- an inner cannula attached to the inner cannula attachment region in such a manner as to block off fluid flow communication between the proximal and distal end portions of the first passage, the inner cannula having proximal and distal end portions, the distal end portion thereof being insertable through the passageway in the outer cannula hub from the proximal end portion thereof and out of the distal end portion thereof; and
- an elastomeric septum having a self-sealing opening therethrough associated with the outer cannula hub for closing communication between the second passage and the outer cannula lumen, the distal end portion of the inner cannula being insertable through the opening through the septum;
- an opening member adapted to open the opening in the septum when positioned therein; and
- moving means for moving the opening member into the opening in the septum to thereby provide fluid flow communication between the second passage and the outer cannula lumen.

* * * * *